United States Patent [19]

McCormack et al.

[11] 4,180,386
[45] Dec. 25, 1979

[54] HEXACOORDINATED TRANSITION METAL COMPOUNDS CONTAINING AT LEAST ONE POLYFLUOROALKYL SUBSTITUENT

[75] Inventors: William B. McCormack; Charles A. Sandy, both of Wilmington, Del.

[73] Assignee: E. I. du pont de Nemours & Company, Wilmington, Del.

[21] Appl. No.: 907,875

[22] Filed: May 19, 1978

[51] Int. Cl.$^2$ .................. C07F 15/00; C07F 15/04; C07F 15/06
[52] U.S. Cl. .................. 44/63; 260/429 J; 260/429 R; 260/439 R; 44/72; 44/76; 44/77; 44/68; 549/3
[58] Field of Search ............ 260/429 J, 429 R, 439 R, 260/329 ME, 332.3 R; 44/68, 72, 76, 77, 63

[56] References Cited

U.S. PATENT DOCUMENTS

| | | | |
|---|---|---|---|
| 2,144,654 | 1/1939 | Gultmann et al. | 202/42 |
| 2,156,918 | 5/1939 | Lyons | 44/68 |

FOREIGN PATENT DOCUMENTS

287192  3/1928  United Kingdom ............ 44/68

OTHER PUBLICATIONS

Cotton et al., "The Tetrameric Structure of Anhydrous Crystalline Cobalt (II) Acetylacetonate," J. Am. Chem. Soc. 86, 2294 (1964).
Fackler et al., Inorg. Chem. 6, 921 (1965).
Hammond et al., Inorg. Chem. 2, 75 (1963).
Gerlach et al., Inorg. Chem. 8, 2293 (1969).
Haszeldine et al., J. Am. Chem. Soc. 609 (1951).
Morris et al., Inorg. Chem. 2, 411 (1963).
Calvin et al., J. Am. Chem. Soc. 67, 2003 (1945).
Reichert et al., Canadian J. Chem. 48, 1362 (1970).
McMillan et al., J. Am. Chem. Soc. 98, 3120 (1976).
Izumi et al., Bull. Chem. Soc. Japan, 483188 (1975).
Unzelman et al., API Reprint No. 47-71, p. 859.
D. P. Graddon, "Polymerization of Transition Metal B-Diketone Chelates", Nature 195, pp. 891-892, 1962.
Biltz et al., "Notes on Acetylactonates", Zert. Anorg. Chem. 40, p. 221, 1904.
D. P. Graddon, "Divalent Transition Metal B-Ketoenolate Complexes as Lewis Acids", Coord. Chem. Rev. 4, pp. 1-28, 1969.
Fenton et al., "Complexes of Bis(hetafluoroacetylacetate) Copper (II) With Some Nitrogen-containing Chelates and Ethylene Glycol, J. Chem. Soc. 1577, 1971.

Primary Examiner—Winston A. Douglas
Assistant Examiner—J. V. Howard
Attorney, Agent, or Firm—James A. Costello

[57] ABSTRACT

Hexacoordinated transition metal compounds, useful as antiknocks, having the structure

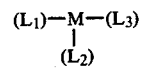

wherein
  M is a divalent metal selected from the group Mn, Fe, Co and Ni,
  $L_1$ and $L_2$ are the same or different chelate-forming β-diketone groups having from 5 to 20 carbon atoms, one or both of $L_1$ and $L_2$ having at least one polyfluoroalkyl group, —$CF_2X$, adjacent to the carbonyl group,
  X is selected from the group H, F, Cl, phenyl, $C_1$–$C_6$ alkyl and $C_nF_{2n}Y$,
  n is 1 to 6,
  Y is H, F, or Cl,
  $L_3$ is a ligand having the structure A-Z-B,
wherein
  A and B are the same or different members of the group —$NH_2$, —$NHR_5$, —$NR_5R_6$, OH, $OR_5$, SH, $SR_5$ and $PR_5R_6$,
  $R_5$ and $R_6$ are the same or different members of the group $C_1$ to $C_4$ alkyl, and
  Z is a divalent hydrocarbyl group having 2 to 10 carbon atoms selected from a member of the group alkylene, phenylene and cycloalkylene, each member providing 2 or 3 carbon atoms between A and B, with the proviso that when Z is phenylene, the number of carbon atoms between A and B is 2.

30 Claims, No Drawings

HEXACOORDINATED TRANSITION METAL COMPOUNDS CONTAINING AT LEAST ONE POLYFLUOROALKYL SUBSTITUENT

BACKGROUND OF THE INVENTION

1. Field of the Invention

This invention relates to hydrocarbon-soluble coordination compounds of divalent manganese, iron, cobalt, and nickel which are useful as antiknock additives in fuels.

2. Description of the Prior Art

One method for improving gasoline antiknock quality (also known as octane quality) is by increasing therein the content of high octane hydrocarbons such as benzene, toluene and the like. This use of high octane hydrocarbon components is relatively uneconomical since they are more valuable as solvents and chemical feedstocks than as gasoline components.

Another method for improving the antiknock quality of gasoline is to add antiknock additives. In the past, tetraalkyllead compounds have been the most popular antiknock additives. The advent of automobiles equipped with catalytic converters has brought the attendant requirement for lead-free gasoline. Thus, there is the corresponding need to develop acceptable antiknock additives to replace those containing lead.

Most lead-free antiknocks suggested in the art are commercially unacceptable because of one or more deficiencies such as high cost, low antiknock activity, hydrolytic-, thermal-, or oxidative-instability, insufficient solubility in gasoline, inadequate volatility, and too-high water solubility. Before discussing the compounds of this invention, a brief summary of some of the prior art teachings will be provided.

British Patent No. 287,192 teaches that β-diketone (such as acetylacetone) compounds of heavy metals such as Fe, Ni, Co, Cr, Th, Cu, Mn, Mo, V and W are useful antiknocks for hydrocarbon fuels. However, in spite of suggestions in the art of processes of stabilizing and solubilizing metal β-diketonates in hydrocarbon fuels, e.g., U.S. Pat. Nos. 2,144,654 and 2,156,918, the metal β-diketonates have not been used commercially as antiknocks.

The utility of the above-mentioned metal β-diketonates as gasoline antiknocks is limited by their low solubility in gasolines and their low volatility. The divalent cobalt compound of acetylacetone, bis-(acetylacetonate)Co(II), has a solubility in gasoline of less than 0.025% at room temperature.

Recent studies have indicated that the acetylacetonates of Mn, Fe, Co, and Ni are polymerized (trimers and tetramers) in the solid state and in nonpolar solvents. The oligomeric nature of these compounds most probably explains their low solubility in gasolines and their low volatility. See Graddon, Nature, 195, 891 (1961), "Polymerization of Transition Metal β-Diketone Chelates"; Cotton et al, J. Am. Chem. Soc., 86, 2294 (1964) "The Tetrameric Structure of Anhydrous Crystalline Cobalt (II) Acetylacetonate"; and Graddon, Coordin. Chem. Rev., 4, 1 (1969), "Divalent Transition Metal β-Keto-Enolate Complexes as Lewis Acids".

From the above, it might appear that a transition metal chelate of β-diketones which would be monomeric in hydrocarbons such as gasoline would have the required solubility, volatility, and antiknock activity. It is known to prepare divalent transition metal chelates of β-diketones which are monomeric in the solid state and in nonpolar solvents by using a β-diketone with bulky groups to preclude self-polymerization of the chelate compounds. Thus, chelate compounds of divalent transition metals with 2,2,6,6-tetramethyl-3,5-heptanedione (dipivaloylmethane, DPM) are reported to be monomeric in the solid state and in non-polar solvents. However, such compounds are not practical as antiknock additives because of their great sensitivity to air oxidation. Fe(DPM)$_2$, for example, is reported to "char immediately on exposure to air"; see Fackler et al, Inorg. Chem., 6, 921 (1965). Mn(DPM)$_2$ "charred immediately on contact with air"; see Hammond et al, Inorg. Chem., 2, 75 (1963). Extreme sensitivity of Co(DPM)$_2$ to oxidation is noted in the Hammond reference supra, p. 76, and by Gerlach et al in Inorg. Chem., 8, pp. 2293 and 2294 (1969).

Metal chelates with β-diketones containing substituents such as fluorine to enhance the volatility of the metal chelates have also been prepared. Haszeldine et al, J. Chem. Soc. 609 (1951), prepared uranium chelates of trifluoroacetylacetone (TFAA) and hexafluoroacetylacetone (HFAA) which could be sublimed without decomposition. Morris et al, Inorg. Chem. 2 411 (1963), prepared dihydrates of hexafluoroacetylacetonates of zinc, nickel, cobalt, manganese and iron, but attempts to dehydrate these complexes by sublimation were unsuccessful.

Considerable work has also been done with copper chelates of fluorinated β-diketones primarily because of the ease of formation of the chelate compounds which are not subject to oxidation as are those of Co$^{++}$ and Fe$^{++}$. See, for example, Calvin et al J. Am. Chem. Soc. 67, 2003 (1945); Reichert et al, Canadian J. Chem. 48, 1362 (1970); Fenton et al J. Chem. Soc. 1577 (1971); and McMillin et al, J. Am. Chem. Soc. 98 3120 (1976).

Fenton et al, in J. Chem. Soc. 1577 (1971) disclose complexes of bis(hexafluoroacetylacetonate)Copper II with some nitrogen bases and glycols. Among the bidentate nitrogen bases, are disclosed ethylenediamine, N,N'- and N,N-dimethylethylenediamine, N,N,N',N'-tetramethylethylenediamine (TMED) and N,N,N',N'-tetramethyl-o-phenylenediamine. Izumi et al, in Bull. Chem. Soc. (Japan) 48 3188 (1975) disclose nitrogen base addition products of bis(hexafluoroacetylacetonato) complexes of Co(II), Ni(II), Cu(II) and Zn(II). The two disclosed bidentate nitrogen bases are 1,10-phenanthroline and 2,2'-bipyridine.

The antiknock activity of the compounds described herein, particularly that of the preferred cobalt compound, is unexpected in view of the teaching in the art that cobalt compounds are not considered to be good antiknocks. Thus, a paper presented at the American Petroleum Institute, Division of Refining, May 14, 1971 (API preprint No. 47-71 at page 859) by Unzelman et al, stated that cobalt compounds are mild antiknocks and that the metal compounds having maximum effectiveness are those with metal atoms bonded to carbon.

On the contrary, the compounds described herein have no metal to carbon bonds and yet they provide effective antiknock performance. In fact, a preferred cobalt compound, as will be detailed more completely in Example 32, is more efficient by about 130% to 240% on a metal weight basis versus a manganese compound of metal to carbon bonds and proven antiknock performance.

SUMMARY OF THE INVENTION

The compounds of this invention are hexacoordinated transition metal complexes having the structure

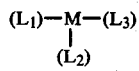

wherein

M is a divalent metal selected from the group Mn, Fe, Co and Ni, $L_1$ and $L_2$ are the same or different chelate-forming $\beta$-diketone groups having from 5 to 20 carbon atoms, one or both of $L_1$ and $L_2$ having at least one polyfluoroalkyl group, $-CF_2X$, adjacent to the carbonyl group, X is selected from the group H, F, Cl, phenyl, $C_1-C_6$ alkyl and $C_nF_{2n}Y$, n is 1 to 6, Y is H, F, or Cl, $L_3$ is a ligand having the structure, A-Z-B, wherein A and B are the same or different members of the group $-NH_2$, $-NHR_5$, $-NR_5R_6$, OH, $OR_5$, SH, $SR_5$ and $PR_5R_6$, $R_5$ and $R_6$ are the same or different members of the group $C_1$ to $C_4$ alkyl, and Z is a divalent hydrocarbyl group having 2 to 10 carbon atoms selected from a member of the group alkylene, phenylene and cycloalkylene, each member providing 2 or 3 carbon atoms between A and B, with the proviso that when Z is phenylene, the number of carbon atoms between A and B is 2.

In X, the $C_1$ to $C_6$ alkyls can be straight or branched; the $C_5$ and $C_6$ alkyls can be cyclic; and $C_nF_{2n}Y$ can be straight or branched. In Z, the alkylene can be straight or branched, and the phenylene and cycloalkylene can be substituted or unsubstituted.

The preferred compounds of this invention have the structure:

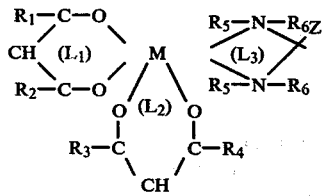

wherein

M is a divalent metal selected from Mn, Fe, Co and Ni, $R_1$, $R_2$, $R_3$, and $R_4$ are each individually selected from $C_1$ to $C_3$ perfluoroalkyl and $C_1$ to $C_6$ alkyl with at least one of $R_1$, $R_2$, $R_3$, and $R_4$ being a perfluoroalkyl group, and $R_5$ and $R_6$ are selected from hydrogen and $C_1$ to $C_4$ alkyl.

The preferred metals are Co and Ni, with Co being most preferred. The preferred compounds are those wherein $R_1$, $R_2$, $R_3$ and $R_4$ are each $CF_3$, wherein $R_5$ and $R_6$ are each $CH_3$, and wherein Z is $-C_2H_4-$. The most preferred compounds of the invention are Co(II) (HFAA)$_2$.TMED and Ni(II) (HFAA)$_2$.TMED. These preferred compounds provide outstanding stability, volatility, solubility in hydrocarbons and antiknock performance.

DETAILS OF THE INVENTION

The compounds of this invention are typically made by contacting the divalent salt of the metal, such as the chloride, nitrate, acetate, etc., with $\beta$-diketones, $L_1$ and $L_2$, and a donor ligand, $L_3$, in the molar ratio of 1:2:1. The reactants can be combined in an aqueous or an organic medium in the presence of a base such as sodium hydroxide. The reaction can be carried out under an inert atmosphere but such is not required. A compound with mixed $\beta$-diketone ligands can be prepared by sequential addition of the two different $\beta$-diketones to the metal salt. Thus, for example, by adding to a basic solution of cobaltous acetate a molar equivalent of acetylacetone (AA), then a molar equivalent of hexafluoroacetylacetone (HFAA), and finally a molar equivalent of N,N,N',N'-tetramethylethylenediamine (TMED), the following compound is obtained: Co(II) (AA) (HFAA).TMED.

The formula, Co(II) (AA) (HFAA).TMED, is a convenient shorthand method of representing the coordination compounds of a divalent metal with $\beta$-diketones and a diamine ligand wherein the AA is the anion of acetylacetone, HFAA is the anion of hexafluoroacetylacetone, TMED is tetramethylethylenediamine, and the Roman Numeral (II) indicates that the metal ion is divalent. The practice of using the initials of the parent $\beta$-ketone in the formula of the coordination compound is widely used in the art; see, for example, the above cited Morris reference. The diamine ligand set off in the formula by a period indicates that it is an intact diamine molecule which is coordinated to the metal ion.

The $\beta$-diketones, $L_1$ and $L_2$, suitable for the preparation of the compounds of this invention are represented by the formula, R-C(O)-CH$_2$-C(O)-R', where R and R' are any $C_1$ to $C_3$ polyfluoroalkyl. The $\beta$-diketones are well-known in the art and can be prepared by known methods. Some $\beta$-diketones such as acetylacetone are available commercially. $\beta$-diketones with perfluoroalkyl groups are also well-known. Haszeldine et al, J. Chem-Soc. 609 (1951) disclose the preparation of trifluoroacetylacetone by Claisen-type condensation of ethyltrifluoroacetate with acetone and the preparation of hexafluoroacetylacetone by the condensation of ethyltrifluoroacetate with trifluoroacetone.

The $\beta$-diketone ligands for the preparation of the present compounds are selected from 2,4-pentanedione, 1,1,1-trifluoro-2,4-pentanedione, 1,1,1,5,5,5-hexafluoro-2,4-pentanedione, 1,1-difluoro-2,4-pentanedione, 1,1,5,5-tetrafluoro-2,4-pentanedione, 1-chloro-1,1-difluoro-2,4-pentanedione, 1,5-dichloro-1,1,5,5-tetrafluoro-2,4-pentanedione, 1-phenyl-1,1-difluoro-2,4-pentanedione, 2,4-hexanedione, 2-methyl-3,4-hexanedione, 1,1,1-trifluoro-2,4-hexanedione, 1,1,1,2,2-pentafluoro-3,5-hexanedione, 1,1,1,2,2,6,6,6-octafluoro-3,5-hexanedione, 1,1,1-trifluoro-5-methyl-2,4-hexanedione, 1,1,1,6,6,6-hexafluoro-2-methyl-3,4-hexanedione, 1,1-difluoro-2,4-hexanedione, 2,2-difluoro-3,5-hexanedione, 1,1,2,2-tetrafluoro-3,5-hexanedione, 1,1,1,5,5-pentafluoro-2,4-hexanedione, 1-chloro-1,1-difluoro-2,4-hexanedione, 1-chloro-1,1,2,2-tetrafluoro-3,5-hexanedione, 2-methyl-3,4-heptanedione, 3,4-heptanedione, 2,6-dimethyl-3,5-heptanedione, 2-methyl-4,6-heptanedione, 2,2,6,6-tetramethyl-3,5-heptanedione, 1,1,1-trifluoro-2,4-heptanedione, 1,1,1,2,2-pentafluoro-3,5-heptanedione, 1,1,1,2,2,6,6,7,7,7-decafluoro-3,5-heptanedione, 1,1,1,2,2,3,3,7,7,7-decafluoro-4,6-heptanedione, 1,1,1,2-tetrafluoro-2-trifluoromethyl-6-methyl-3,5-heptanedione, 1,1,1,2,6,7,7,7-octafluoro-2,6-ditrifluoromethyl-3,5-heptanedione, 1,1-difluoro-2,4-heptanedione, 1-chloro-1,1-difluoro-2,4-heptanedione, 3,3-difluoro-4,6-heptanedione, 1-chloro-1,1,2,2-tetrafluoro-3,5-heptanedione, 1,1,2,2,6,6,7,7-octafluoro-3,5-heptanedione, 1,7-dichloro-1,1,2,2,6,6,7,7-octafluoro-3,5-heptanedione, 2-methyl-4,6-octanedione, 2,8-dimethyl-4,6-nonanedione, 2,4-decanedione, benzoylacetone and benzoyltrifluoroacetone.

The two β-diketone ligands used in the compounds of this invention can be the same or different provided that at least one of the β-diketone ligands contains at least one polyfluoroalkyl group. The presence of a polyfluoroalkyl group in at least one of the β-diketone ligands is required for good antiknock activity. The compounds will preferably contain perfluoroalkyl groups on both β-diketones. The most preferred compounds are those made from β-diketones containing two perfluoroalkyl groups such as 1,1,1,5,5,5-hexafluoro-2,4-pentanedione, which is commonly referred to as hexafluoroacetylacetone (HFAA). Hexafluoroacetylacetone provides highly stable volatile coordination compounds which are excellent antiknock compounds.

Ligand, $L_3$, is represented by the formula A-Z-B where A, Z and B are as defined. The provision in the hydrocarbyl group, Z, of 2 to 3 carbon atoms between A and B is important to provide desired stability by formation of a 5 to 6 membered ring upon chelation of $L_3$ with the metal ion. The hydrocarbyl group, Z, can be in an alkylene group such as ethylene, propylene, or alkyl-substituted ethylene or propylene, a cycloalkylene or a phenylene group such as 1,2-phenylene.

Representative diamines include ethylenediamine, 1,2-propylenediamine, 1,3-propylenediamine, 2-methyl-1,3-diaminepropane, 2,2-dimethyl-1,3-diaminopropane, and orthophenylenediamine. The following methyl substituted diamines, including the corresponding ethyl-, propyl- and butyl-substituted diamines, are useful to make the compounds of this invention: N-methylethylenediamine, N,N-dimethylethylenediamine, N,N'-dimethylethylenediamine, N,N,N'-trimethylethylenediamine, N,N,N',N'-tetramethylethylenediamine, N-methyl-1,2-propylenediamine, N,N-dimethyl-1,2-propylenediamine, N,N'-dimethyl-1,2-propylenediamine, N,N,N'-trimethyl-1,2-propylenediamine, N,N,N',N'-tetramethyl-1,2-propylenediamine, N-methyl-1,3-propylenediamine, N,N-dimethyl-1,3-propylenediamine, N,N-dimethyl-1,3-propylenediamine, N,N,N'-trimethylpropylenediamine, N,N,N',N'-tetramethyl-1,3-propylenediamine, N-methyl-2-methyl-1,3-diaminopropane, N,N-dimethyl-2-methyl-1,3-diaminopropane, N,N'-dimethyl-2-methyl-1,3-diaminopropane, N,N,N'-trimethyl-2-methyl-1,3-diaminopropane, N,N,N',N'-tetramethyl-2-methyl-1,3-diaminopropane, N-methyl-2,2-dimethyl-1,3-diaminopropane, N,N-dimethyl-2,2-dimethyl-1,3-diaminopropane, N,N'-dimethyl-2,2-dimethyl-1,3-diaminopropane, N,N,N'-trimethyl-2,2-dimethyl-1,3-diaminopropane, N,N,N'-tetramethyl-2,2-dimethyl-1,3-diaminopropane, N-methyl-o-phenylenediamine, N,N-dimethyl-o-phenylenediamine, N,N'-dimethyl-o-phenylenediamine, N,N,N'-trimethyl-o-phenylenediamine, N,N,N'-N'-tetramethyl-o-phenylenediamine and the like. The preferred diamines are N,N,N',N'-tetramethylethylenediamine, N,N,N',N'-tetramethyl-1,2-propylenediamine, N,N,N',N'-tetramethyl-1,3-propylenediamine and N,N,N',N'-tetramethyl-2,2-dimethyl-1,3-diaminopropane. $L_3$ ligands, other than diamines, include aminoethers, aminothioethers, ethers, thioethers and phosphines. Representative compounds include dimethylether of ethylene glycol, dimethylether of propyleneglycol, 1-methoxy-2-(dimethylamino)ethane, 1-methylthio-2-(dimethylamino)ethane, 1,2-di(ethylthio)ethane, 1,2-di(dimethylphosphino)ethane and the like.

In addition to utility as antiknock additives for fuels, the compounds of this invention are also useful to introduce the complexed metals into hydrocarbon systems. Because of the intense color of many of these compounds, they can be used to color organic systems such as gasoline. They can also be used as combustion control additives for hydrocarbon fuels, such as for control of carbon formation in the combustion of fuel oils. They are also useful as octane requirement increase control additives in internal combustion engines.

Not all of the compounds of this invention exhibit the same degree of stability, solubility, volatility and antiknock performance. All compounds are, however, stable upon exposure to air. They are soluble in hydrocarbon fuels to provide concentrations of metal per gallon sufficient to improve antiknock performance. They are volatile as shown by thermal gravimetric Analysis (TGA) in that at least 20 mg of the compound is volatilized by the time 250° C. is reached by raising the temperature 5° C. per minute with nitrogen passed over the sample at 40 cc per minute.

The cobalt, nickel and manganese compounds are more stable in fuel than are the iron compounds. In fact, care must be taken to properly stabilize the iron compounds or they will quickly react with impurities in the fuel to lose their antiknock activity and become ineffectual for that purpose. Alternatively, of course, such iron compounds can be employed in fuels which are free of the reaction-causing impurities or they can be used within several hours after introduction into the fuel.

The hydrocarbon fuel to which the compounds are added comprises gasoline or a mixture of hydrocarbons boiling in the gasoline range which is normally about 32° C. to 220° C. The base fuel can consist of straight-chain or branched-chain paraffins, cycloparaffins, olefins and aromatic compounds or any mixture of such hydrocarbons obtainable from straight run naphtha, polymer gasoline, natural gasoline, thermally or catalytically cracked hydrocarbon stocks and catalytically reformed stocks. The gasoline can also contain conventional gasoline additives such as antiknock compounds, dyes, antioxidants, anti-icing agents, rust inhibitors, detergents, anti-preignition agents, intake valve deposit control additives, antistatic agents, stabilizers and the like.

The compounds of this invention can be added directly to gasoline. They also can be added as concentrates in suitable liquid organic solvents such as alcohols and hydrocarbons. Particularly suitable solvents are those hydrocarbons boiling in the gasoline and light hydrocarbon range such as hexane, isooctane, kerosene, toluene and xylene. The concentrate can contain from about 5% to 50%, preferably from about 10% to 40% by weight of the compounds of this invention.

The amount of compound incorporated into gasoline will depend upon the antiknock quality of the base gasoline and the improvement desired. The compounds of this invention provide antiknock improvements when used in amounts to provide about 0.01 gram of metal per gallon. Preferably, the metal concentration will be from about 0.02 to 3 grams of metal per gallon, more preferably from about 0.025 to 0.5 gram of metal per gallon.

The following Examples illustrate the invention.

EXAMPLES

The Research Method (ASTM D-909) and the Motor Method (ASTM D-357) were used to determine the antiknock improving performance of the compounds of the invention. Generally, the Research Octane Number (RON) is considered to be a better guide of antiknock quality when vehicles are operated under mild conditions associated with low speeds while the Motor Octane Number (MON) is a better indicator when vehicles are operated at high engine speed or under heavy load conditions. For many engine operating conditions, some intermediate value between the Research and the Motor Octane Numbers such as an average, (RON+MON)/2, is of most interest.

The fuel samples were knock-rated in duplicate and the results are reported as averages of these ratings expressed to the nearest tenth of an octane number. The gasolines used were representative of commercially available lead-free gasolines. The specifications of the three gasolines are given below.

| GASOLINE-SPECIFICATIONS | Fuel A °C. | Fuel B °C. | Fuel C °C. |
|---|---|---|---|
| ASTM D-86 Distillation | 33 | 33 | 38 |
| Initial Boiling Point | 44 | 44 | 53 |
| 5% | | | |
| 10% | 52 | 52 | 62 |
| 20% | 67 | 66 | — |
| 30% | 84 | 80 | 97 |
| 40% | 98 | 93 | — |
| 50% | 109 | 106 | 122 |
| 60% | 119 | 117 | — |
| 70% | 132 | 129 | 144 |
| 80% | 146 | 144 | — |
| 90% | 169 | 167 | 179 |
| 95% | 188 | 183 | 201 |
| Max. Temp. | 202 | 209 | 219 |
| Recovery, Vol. % | 98.0 | 99.0 | 98.0 |
| Residue, Vol. % | 1.0 | 1.0 | 1.0 |
| ASTM D-287 Gravity 60/60 F | 0.737 | 0.738 | — |
| ASTM D-323 Reid Vapor Pressure, lb | 9.9 | 9.9 | 7.9 |
| ASTM D-525 Induction Period | No Break | No Break | No Break |
| ASTM D-3120 Sulfur, wt % | 0.014 | 0.038 | 0.034 |
| ASTM D-1319 Hydrocarbon Types | | | |
| Saturates, Vol. % | 73 | 68 | 61 |
| Olefins, Vol. % | 3 | 8 | 8 |
| Aromatics, Vol. % | 24 | 24 | 31 |
| ASTM D-909 Research Octance No. | 91.4 | 89.3 | 91.4 |
| ASTM-D D-357 Motor Octane No. | 81.8 | 83.8 | 82.0 |
| (R + M)/2 Octane No. | 86.6 | 86.6 | 86.7 |

EXAMPLE 1

Bis(hexafluoroacetylacetonato)cobalt(II)tetramethylethylenediamine, Co(II) (HFAA)$_2$.TMED To a 2-liter reaction flask equipped with a mechanical stirrer, a condenser, a gas inlet tube and an addition funnel, 700 ml of deionized water was added. The water was sparged for ½ hour with nitrogen at reflux and then cooled to room temperature. Hexafluoroacetylacetone (HFAA), $CF_3$—C(O)—$CH_2$—C(O)—$CF_3$, was then added in an amount of 104 g over a period of 15 minutes. A temperature rise of 5° C. was noted. After stirring for 15 minutes, 20.4 g of sodium hydroxide dissolved in 70 ml of water was added over 17 minutes. Cobaltous chloride solution (59.5 g of $CoCl_2.6H_2O$ dissolved in 280 ml of water) was added over 15 minutes. Yellow precipitate formed initially and gradually turned light green. After stirring for 1 hour, 29 g of tetramethylethylenediamine (TMED), $(CH_3)_2NCH_2CH_2N(CH_3)_2$, was added. The color of the precipitate changed from light green to brownish-yellow. After stirring for an additional 2½ hours, the reaction mass was filtered and the solids washed with water. The filter cake (89.6 g) was heated with 450 ml. of toluene and filtered. Removal of the solvent from the filtrate provided 78 g (53% yield) of rust-colored product which melted at 100° to 101.5° C. A portion of the product was recrystallized from petroleum ether. Elemental analysis: Calculated for $Co(C_{16}H_{18}N_2O_4F_{12})$: C, 32.6; H, 3.1; N, 4.8; F, 38.7; Co, 10.0. Found: C, 32.5; H, 2.9; N, 4.7; F, 38.2; Co, 10.2.

Thermogravimetric analyses of Co(II) (HFAA)$_2$.TMED were carried out in a Du Pont 990 Thermal Analyzer coupled to a Du Pont 951 Thermogravimetric Analyzer. In these characterizations a sample (about 20 mg) was heated over a temperature range of 25° to 500° C. at a heating rate increase of 5° C. per minute with nitrogen or air as the carrier gas at a gas flow rate of 40 ml per minute. The loss in sample weight was recorded continuously.

The thermogravimetric analysis carried out with nitrogen as the carrier gas provided information on the volatility and thermal stability of the compound. The analysis carried out with air as the carrier gas, in addition to volatility and thermal stability information provided information on the oxidation stability of the compound; thermal or oxidative instability being indicated by discontinuous weight loss and incomplete volatilization of the metal residues. The following data demonstrate the good volatility, and thermal and oxidative stability of Co(II) (HFAA)$_2$.TMED.

| THERMOGRAVIMETRIC ANALYSIS Co(II) (HFAA)$_2$.TMED | | | |
|---|---|---|---|
| Carrier Gas = Nitrogen | | Carrier Gas = Air | |
| Sample Wt. 18.3 mg | | Sample Wt. 23.4 | |
| Temp. °C. | Wt. % Volatilized | Temp. °C. | Wt. % Volatilized |
| 75 | 0.0 | 75 | 0.0 |
| 90 | 0.3 | 90 | 0.4 |
| 100 | 1.1 | 100 | 0.8 |
| 110 | 2.7 | 110 | 1.2 |
| 120 | 6.0 | 125 | 3.8 |
| 125 | 7.6 | 150 | 16.2 |
| 135 | 12.6 | 160 | 25.2 |
| 140 | 15.3 | 170 | 42.3 |
| 150 | 22.4 | 175 | 50.8 |
| 160 | 34.4 | 185 | 78.6 |
| 170 | 51.9 | 190 | 91.5 |
| 175 | 61.7 | 200 | 100.0 |
| 185 | 89.1 | | |
| 187 | 100.0 | | |

EXAMPLE 2

Bis(Pivaloyltrifluoroacetonato)cobalt(II)tetramethylethylenediamine, Co(II) (PTFA)$_2$.TMED To a 2-liter reaction flask equipped with a mechanical stirrer, a condenser, a gas inlet tube and an addition funnel, 560 ml of denatured ethyl alcohol was added. The alcohol was heated to reflux and sparged with nitrogen and allowed to cool. Pivaloyltrifluoroacetone (PTFA), $(CH_3)_3C—C(O)—CH_2—C(O)—CF_3$, was then added in an amount of 78.5 grams over 10 minutes. Sodium hydroxide solution (16.3 g of sodium hydroxide dissolved in 56 ml water) was then added over a period of 19 minutes. A temperature rise of 5° C. was noted. After stirring for 15 minutes, cobaltous chloride solution (47.6 g $CoCl_2.6H_2O$ dissolved in 224 ml of water) was added over 17 minutes. Dark red precipitate formed. The reaction mixture was stirred for 1 hour and 23.2 g of tetramethylethylenediamine (TMED), $(CH_3)_2NCH_2CH_2N(CH_3)_2$, was added over 15 minutes causing the temperature to rise 2.5° C. After stirring for an additional 2½ hours, the reaction mass was filtered and the precipitate washed with water. The product was extracted into 35 ml of toluene by stirring, then filtered. Removal of toluene provided 81.5 g of red, sticky solid. Recrystallization from petroleum ether provided 39 g of orange solid. The orange solid appeared to melt at 157° C. (no solid remaining but no liquefaction) and was completely liquid at 196° C. Elemental analysis: Calculated for $Co(C_{22}H_{36}O_4N_2F_6)$: C, 46.7; H, 6.4; N, 5.0; F, 20.2; Co, 10.4. Found: C, 47.4; H, 6.0; N, 5.1; F, 19.8; Co, 10.8.

Thermogravimetric analyses of Co(II) $(PTFA)_2$.TMED were carried out as previously described and the results, summarized below, demonstrate its good volatility and oxidative and thermal stability.

| THERMOGRAVIMETRIC ANALYSIS Co(II) $(PTFA)_2$ . TMED | | | |
|---|---|---|---|
| Carrier Gas = Nitrogen | | Carrier Gas = Air | |
| Sample Wt. 17.2 mg | | Sample Wt. 19.9 mg | |
| Temp. °C. | Wt. % Volatilized | Temp. °C. | Wt. % Volatilized |
| 75 | 0.0 | 75 | 0.0 |
| 100 | 1.2 | 100 | 0.5 |
| 125 | 1.7 | 125 | 1.0 |
| 150 | 3.5 | 150 | 2.5 |
| 175 | 11.0 | 175 | 9.5 |
| 200 | 33.7 | 200 | 29.6 |
| 210 | 51.2 | 210 | 47.8 |
| 220 | 76.7 | 220 | 72.7 |
| 225 | 93.0 | 225 | 87.4 |
| 233 | 100.0 | 233 | 100.0 |

EXAMPLE 3

Bis(trifluoroacetylacetonato)cobalt(II)tetramethylethylenediamine, Co(II) $(TFAA)_2$.TMED To a 3-liter reaction flask equipped with a mechanical stirrer, a condenser, a gas inlet tube and an addition funnel, 1120 ml of deionized water was added. The water was heated to reflux and sparged with nitrogen and cooled. Trifluoroacetylacetone (TFAA), $CF_3—C(O)—CH_2—C(O)—CH_3$, 123.3 g, was added and after stirring for 15 minutes, a solution of sodium hydroxide (32.7 g of sodium hydroxide dissolved in 112 ml of water) was added over a period of 20 minutes. A temperature rise of 4° C. was noted. Cobaltous chloride solution (95.2 g of $CoCl_2.6H_2O$ dissolved in 448 ml water) was added over 25 minutes causing a formation of light brown precipitate. After stirring for 1 hour, tetramethylethylenediamine (TMED), $(CH_3)_2N—CH_2—CH_2—N(CH_3)_2$ was added. The color of the precipitate changed to green. The reaction mixture was stirred for 2½ hours and filtered. The precipitate was washed with water and dried on a porous plate. The product was extracted into 900 ml of toluene by stirring at room temperature, then filtered. Evaporation of toluene from the filtrate provided 58.6 g (30% yield) of the product. The product was recrystallized from petroleum either to provide a reddish orange solid, m.p. 85.5° C. Elemental analysis: Calculated for $Co(C_{16}H_{24}N_2O_4F_6)$: C, 39.9; H, 5.0; N, 5.2; F, 23.7; Co, 12.2. Found: C, 40.2; H, 4.9; N, 5.8; F, 22.4; Co, 12.3.

Thermogravimetric analyses of Co(II) $(TFAA)_2$.TMED were carried out as previously described and the results, summarized below, demonstrate good volatility and oxidative and thermal stability.

| THERMOGRAVIMETRIC ANALYSIS Co(II) $(TFAA)_2$ . TMED | | | |
|---|---|---|---|
| Carrier Gas = Nitrogen | | Carrier Gas = Air | |
| Sample Wt. 20.1 mg | | Sample Wt. 26.2 mg | |
| Temp. °C. | Wt. % Volatilized | Temp. °C. | Wt. % Volatilized |
| 75 | 0.0 | 75 | 0.0 |
| 90 | 0.2 | 100 | 0.0 |
| 100 | 0.5 | 125 | 2.2 |
| 110 | 1.0 | 150 | 8.0 |
| 125 | 3.0 | 160 | 12.2 |
| 135 | 5.5 | 170 | 18.0 |
| 150 | 13.0 | 175 | 22.2 |
| 165 | 24.0 | 180 | 27.5 |
| 175 | 36.3 | 190 | 40.9 |
| 190 | 61.4 | 200 | 61.8 |
| 200 | 83.8 | 210 | 86.7 |
| 205 | 95.0 | 218 | 100.0 |
| 208 | 100.0 | | |

EXAMPLES 4 to 19

The following compounds were prepared by sequential addition of a perfluoroalkyl-containing β-diketone and a diamine ligand to the metal salts in the presence of a base. Each of the compounds is stable in air and is soluble in hydrocarbons. Thermogravimetric analysis (TGA) data indicate that each of the compounds is substantially completely volatilized by about 250° C. Each of the compounds is stable in hydrocarbon solutions indefinitely. With the iron compounds (Examples 14,15 and 16), the solutions in a hydrocarbon solvent or other organic solvent are stable provided the solvents are free of peroxides. In the presence of the peroxides, the iron compounds appear to undergo some reaction to precipitate iron compounds of unknown composition.

In the Table, these abbreviations are used: PTFA=pivaloyltrifluoroacetone; HFAA=hexafluoroacetylacetone; TFAA=trifluoroacetylacetone; TMPD=N,N,N',N'-tetramethyl-1,3-propylenediamine; HMPD=N,N,N',N'-2,2-hexamethylpropylenediamine; TMED=N,N,N',N'-tetramethylethylenediamine; ED=ethylenediamine; and TGA=Thermogravimetric Analysis. The temperatures are those recorded from the start of volatilization until the end of the test.

| | | | | | TGA | |
|---|---|---|---|---|---|---|
| Ex. | $M^{2+}$ | Diketone Ligand | Diamine Ligand | m.p. °C. | Temp. °C. | % Volatilized |
| 4 | Co | HFAA | TMPD | 128–129 | 110–187 | 100 |
| 5 | Co | HFAA | HMPD | 96.0–97.5 | 110–190 | 100 |
| 6 | Mn | HFAA | TMED | 83.0–84.0 | 110–175 | 99 |
| 7 | Mn | PTFA | TMED | — | — | — |

-continued

| Ex. | $M^{2+}$ | Diketone Ligand | Diamine Ligand | m.p. °C. | TGA Temp. °C. | % Volatilized |
|---|---|---|---|---|---|---|
| 8 | Mn | TFAA | TMED | 96.5–97.5 | — | — |
| 9 | Mn | HFAA | TMPD | 95.0–96.0 | 100–250 | 100 |
| 10 | Mn | HFAA | ED | — | — | — |
| 11 | Mn | TFAA | ED | — | — | — |
| 12 | Mn | HFAA | HMPD | 86.0–87.5 | 115–225 | 91 |
| 13 | Mn | PTFA | ED | — | — | — |
| 14 | Fe | TFAA | TMED | 98–99 | 115–210 | 95 |
| 15 | Fe | HFAA | TMED | 32–83 | 125–192 | 100 |
| 16 | FE | HFAA | HMPD | 87–89 | — | — |
| 17 | Ni | TFAA | TMED | 78.0–78.5 | 105–210 | 100 |
| 18 | Ni | HFAA | TMED | 128–130 | 125–186 | 100 |
| 19 | Ni | HFAA | HMPD | 116–117 | — | — |

EXAMPLE 20

(Acetylacetonatohexafluoroacetylacetonato)cobalt(II)-tetramethylethylenediamine, Co(II) (AA) (HFAA).TMED This Example concerns compounds of the invention wherein one β-diketone contains perfluoroalkyl substituents and the other β-diketone does not.

Into a 1-liter reaction flask equipped with an agitator, a condensor, a thermometer, an addition funnel and a gas inlet tube, were placed cobaltous acetate (12.4 g, 0.05 mole) and 200 ml of water. The mixture was purged with nitrogen gas for 15 minutes then cooled to 5° C. and a solution of 2,4-pentanedione (acetylacetone, AA) (5.0 g, 0.05 mole) in 25 ml of absolute ethanol was added dropwise. After stirring for 15 minutes, 2.6 g (0.025 mole) of sodium carbonate was added. The reaction mixture was allowed to warm to room temperature and hexafluoroacetylacetone (HFAA) (10.4 g, 0.05 mole) dissolved in 25 ml of absolute ethanol was added dropwise. The reaction mixture was orange in color. Sodium carbonate (2.6 g, 0.025 mole) was then added followed by N,N,N',N'-tetramethylethylenediamine (TMED) (11.6 g; 0.10 mole) dissolved in 200 ml of benzene. The reaction mixture was stirred for 1 hour. The benzene phase was separated and washed with 50 ml of water. Removal of benzene provided 22.5 g (93.5% yield) of red compound which melted at 49°–50° C. A one-gram sample was sublimed (50° C. and 0.2 min pressure) to provide a brick-red solid, m.p. 50°–51° C. Elemental analyses: Calculated for $CoC_{16}H_{24}O_4F_6H_2$%: C, 39.9; H, 5.0; N, 5.8; F, 23.7; Found: C, 39.2; H, 5.0; N, 5.8; F, 23.2. Thermogravimetric analysis indicated smooth volatilization with 5% volatilization at 123° C. and 100% volatilization at 200° C.

High Resolution Mass Spectrometry (HRMS) of a sample introduced directly into the ionization chambers at 50° C. showed an intense peak corresponding to 481.0970 mass number which corresponded to the molecular weight of 481.303 for the compound with mixed β-diketone ligands. On the basis of its sharp melting point (50°–51° C., unchanged on sublimation), elemental analysis, smooth TGA curve and mass spectrometric analysis, the compound was identified as Co(II) (AA) (HFAA).TMED and not a physical mixture of Co(II) (AA)₂.TMED, Co(II) (HFAA)₂.TMED, and Co(II) (AA) (HFAA).TMED.

When the sample made by the procedure of this Example was preheated to 200° C. before ionization in the mass spectrometer, intense fragments from Co(II) (AA)₂.TMED and Co(II)(HFAA)₂.TMED were found thus indicating that compounds with mixed β-diketone ligands undergo ligand exchange at 200° C.

EXAMPLE 21

(Isovalerylacetonetrifluoroacetylacetone)cobalt(II)tetramethylethylenediamine, Co(II) (IVA) (TFAA).TMED By the procedure substantially as described above except for the substitution of 2-methyl-4,6-heptanedione (isovalerylacetone, IVA) for acetylacetone and of trifluoroacetylacetone (TFAA) for hexafluoroacetylacetone, Co(II) (IVA) (TFAA).TMED was prepared. Elemental analysis: Calculated for $CoC_{19}H_{33}O_4N_2F_3$: C, 48.6; H, 7.1; N, 6.0 and F, 12.1. Found: C, 46.9; H, 6.8; N, 5.9 and F, 12.2. The compound is a red-brown liquid which is very volatile (93% volatilization between 100° C. to 130° C.).

EXAMPLES 22 to 31

Antiknock performances of the compounds of this invention were determined by the Research and the Motor Methods as described. The iron compound of Example 25 was tested for antiknock activity before it reacted with fuel impurities, i.e., it was tested within several hours of its introduction into the fuel. The results obtained with the three previously described gasolines are summarized below.

| Ex. No. / Fuel | Metal/ Gallon (G) | Research (R) | Motor (M) | (R + M)/2 |
|---|---|---|---|---|
| 22/ Fuel A | Co(II) (HFAA)₂TMED | | | |
| | 0.025 | 1.7 | 0.6 | 1.1 |
| | 0.05 | 2.6 | 1.1 | 1.8 |
| | 0.10 | 3.0 | 1.2 | 2.1 |
| | 0.15 | 3.6 | 1.5 | 2.5 |
| | 0.20 | 4.2 | 1.9 | 3.2 |
| | 0.25 | 4.5 | 1.9 | 3.2 |
| 23/ Fuel A | Co(II)(TFAA)₂.TMED | | | |
| | 0.025 | 1.5 | 0.1 | 0.8 |
| | 0.05 | 2.1 | 0.6 | 1.3 |
| | 0.10 | 2.7 | 1.0 | 1.8 |
| | 0.15 | 3.2 | 1.4 | 2.3 |
| | 0.20 | 3.6 | 1.8 | 2.7 |
| | 0.25 | 4.0 | 2.0 | 3.0 |
| 24/ Fuel A | Co(II) (PTFA)₂.TMED | | | |
| | 0.025 | 1.2 | 0.3 | 0.7 |
| | 0.05 | 0.2 | 0.3 | 0.2 |
| | 0.10 | −0.3 | 0.6 | 0.1 |
| | 0.15 | 1.9 | 0.7 | 1.3 |
| | 0.20 | 3.2 | 1.8 | 2.5 |
| | 0.25 | 3.5 | 1.7 | 2.6 |
| 25/ Fuel B | Fe(II) (TFAA)₂.TMED | | | |
| | 0.025 | 0.0 | 0.5 | 0.3 |
| | 0.05 | 0.3 | 0.3 | 0.3 |
| | 0.10 | −0.5 | 0.1 | −0.2 |
| | 0.20 | 0.9 | 0.2 | 0.6 |
| 26/ Fuel B | Ni(II) (TFAA)₂.TMED | | | |
| | 0.025 | 0.6 | 0.0 | 0.3 |
| | 0.05 | 1.1 | 0.3 | 0.7 |
| | 0.10 | 1.9 | 0.6 | 1.3 |
| | 0.20 | 2.6 | 0.9 | 1.8 |
| 27/ Fuel B | Co(II) (AA) (HFAA).TMED | | | |
| | 0.025 | 1.1 | 0.5 | 0.8 |
| | 0.05 | 1.5 | 0.8 | 1.2 |

ANTIKNOCK PERFORMANCE

| Ex. No. Fuel | Metal/ Gallon (G) | Increase in Octane Number (ΔON) | | |
|---|---|---|---|---|
| | | Research (R) | Motor (M) | (B + M)/2 |
| | 0.10 | 2.3 | 1.1 | 1.7 |
| | 0.15 | 2.9 | 1.3 | 2.1 |
| | 0.20 | 3.3 | 1.5 | 2.4 |
| | 0.25 | 4.1 | 1.8 | 2.9 |
| 28/ Fuel C | Mn(II) (HFAA)$_2$.TMED | | | |
| | 0.025 | 0.5 | 0.3 | 0.4 |
| | 0.05 | 1.0 | 0.5 | 0.8 |
| | 0.10 | 1.5 | 1.0 | 1.3 |
| | 0.15 | 1.8 | 1.2 | 1.5 |
| | 0.20 | 2.0 | 1.1 | 1.5 |
| | 0.25 | 2.1 | 1.6 | 1.9 |
| | 0.30 | 2.2 | 1.8 | 2.0 |
| 29/ Fuel C | Mn(II) (PTFA)$_2$.TMED | | | |
| | 0.025 | 0.3 | 0.1 | 0.2 |
| | 0.05 | 0.6 | 0.4 | 0.5 |
| | 0.10 | 0.7 | 0.5 | 0.6 |
| | 0.15 | 1.2 | 0.6 | 0.9 |
| | 0.20 | 1.3 | 0.7 | 1.0 |
| | 0.25 | 1.4 | 0.8 | 1.1 |
| | 0.30 | 1.4 | 0.7 | 1.2 |
| 30/ Fuel C | Mn(II) (TFAA)$_2$.TMED | | | |
| | 0.025 | 0.3 | 0.1 | 0.2 |
| | 0.05 | 0.7 | 0.2 | 0.5 |
| | 0.10 | 1.0 | 0.5 | 0.8 |
| | 0.15 | 1.0 | 0.6 | 0.8 |
| | 0.20 | 0.9 | 0.7 | 0.8 |
| | 0.25 | 1.0 | 0.5 | 0.8 |
| | 0.30 | 1.1 | 0.7 | 0.9 |
| 31/ Fuel C | Co(II) (HFAA)$_2$.TMED | | | |
| | 0.025 | 1.7 | 0.9 | 1.3 |
| | 0.05 | 2.2 | 1.4 | 1.8 |
| | 0.10 | 2.8 | 1.9 | 2.4 |
| | 0.15 | 3.3 | 2.1 | 2.7 |
| | 0.20 | 3.7 | 2.4 | 3.1 |
| | 0.25 | 4.1 | 2.6 | 3.3 |
| | 0.30 | 4.1 | 2.6 | 3.3 |

The above results show that each of the compounds of this invention provides improvements in the octane numbers in each of the three gasolines. The improvements provided by the cobalt and the nickel compounds are outstanding.

EXAMPLE 32 INCLUDING COMPARISONS

The compound of Example 1, Co(II) (HFAA)$_2$.TMED, was compared in antiknock efficiency with two commercial metal-containing antiknock compounds: tetraethyllead, and methylcyclopentadienylmanganesetricarbonyl, also known as "MMT". The comparison was made in a commercial lead-free gasoline (Fuel C) whose specifications were provided earlier. The knock ratings were carried out by ASTM D-909 (Research) and ASTM D-357, (Motor Methods) in duplicates, and the results are expressed in terms of octane number increase (ΔON) to the nearest tenth (0.1) of the octane numbers. The results are also expressed in terms of (R+M)/2, which values show good correlation with road octane improvements.

ANTIKNOCK PERFORMANCE (Comparison)

| Gms of Metal per Gallon | Octane Number Increase (ΔON) | | |
|---|---|---|---|
| | Research (R) | Motor (M) | (R + M)/2 |
| Antiknock Additive = Tetraethyllead (as Motor Mix) | | | |
| 0.025 | 0.3 | 0.2 | 0.3 |
| 0.05 | 0.3 | 0.2 | 0.3 |
| 0.10 | 0.8 | 0.5 | 0.7 |
| 0.15 | 1.0 | 0.6 | 0.8 |
| 0.20 | 1.5 | 1.0 | 1.3 |
| 0.25 | 1.7 | 1.5 | 1.6 |
| 0.30 | 1.9 | 1.6 | 1.8 |
| Antiknock Additive = methylcyclopentadienyl-manganesetricarbonyl (Comparison) | | | |
| 0.025 | 0.7 | 0.6 | 0.7 |
| 0.05 | 1.1 | 0.6 | 0.9 |
| 0.10 | 1.9 | 1.1 | 1.5 |
| 0.15 | 2.4 | 1.2 | 1.8 |
| 0.20 | 2.6 | 1.3 | 2.0 |
| 0.25 | 3.0 | 1.6 | 2.3 |
| 0.30 | 3.1 | 1.8 | 2.5 |

ANTIKNOCK PERFORMANCE (Example 32)

| Gms of Metal per Gallon | Octane Number Increase (ΔON) | | |
|---|---|---|---|
| | Research (R) | Motor (M) | (R + M)/2 |
| Antiknock Additive = Co(II) (HFAA)$_2$.TMED (Invention Compound) | | | |
| 0.025 | 1.7 | 0.9 | 1.3 |
| 0.05 | 2.2 | 1.4 | 1.8 |
| 0.10 | 2.8 | 1.9 | 2.4 |
| 0.15 | 3.3 | 2.1 | 2.7 |
| 0.20 | 3.7 | 2.4 | 3.1 |
| 0.25 | 4.1 | 2.6 | 3.3 |
| 0.30 | 4.1 | 2.6 | 3.4 |

The above results demonstrate the outstanding and unexpected antiknock efficiency of the invention compound.

The Research Octane Number data show that 0.025 g per gallon of cobalt as Co(II) (HFAA)$_2$.TMED provides an increase of 1.7 octane number whereas the same concentration of manganese as MMT provides an increase of 0.7 octane number and of lead as tetraethyllead provides an increase of 0.3 octane number. Expressed in another way: at 0.025 g per gallon treating level, cobalt in the compounds of this invention has an efficiency which is 243% greater than manganese and 563% greater than lead.

The following Table summarizes the superiority of the cobalt compounds of this invention in improving the Research Octane Numbers over the two commercially used antiknock compounds. Similar comparisons can be made for Motor and (R+M)/2 Octane increases.

| Comparative Research Octane Number Increase | | |
|---|---|---|
| Gms of Metal per Gallon | Percent Efficiency of Cobalt [1] Over | |
| | Manganese[2] | Lead[3] |
| 0.025 | 243 | 563 |
| 0.05 | 200 | 732 |
| 0.10 | 147 | 350 |
| 0.15 | 138 | 280 |
| 0.20 | 142 | 247 |
| 0.25 | 137 | 241 |
| 0.30 | 132 | 216 |

[1]Cobalt as Co(II) (HFAA)$_2$.TMED
[2]Manganese as methylcyclopentadienylmanganesetricarbonyl
[3]Lead as tetraethyllead The above Table shows the superiority of cobalt over manganese and lead. It also shows that the degree of superiority increases with decreasing concentration of the metals. Enhanced superiority at low metal concentration is important since the desired octane number increase can be achieved with a lesser amount of cobalt than either manganese or lead with attendant decrease in difficulties generally believed to be associated with use of metal-containing additives in gasoline.

EXAMPLE 33

The compound of Example 1, Co(II) (HFAA)$_2$.TMED, was tested as an antiknock additive in a Road Octane Test carried out according to the Modified Uniontown Method (CRC F-28-70). These tests used a fleet of nine automobiles identified as follows:

| Automobile* | No. Cyl. | Comp. Ratio | Displ. cu in | Brake Horse-power | Carb. bbl. |
|---|---|---|---|---|---|
| Oldsmobile Cutlass | 8 | 8.0 | 350 | 170 | 4 |
| Chevrolet Impala | 8 | 8.5 | 305 | 145 | 2 |
| Ford LTD | 8 | 8.0 | 351 M | 161 | 2 |
| Ford Granada | 8 | 8.0 | 302 | 129 | 2 |
| Pontiac Catalina | 8 | 7.6 | 400 | 180 | 4 |
| Plymouth Fury | 8 | 8.5 | 318 | 145 | 2 |
| Chevrolet Nova | 6 | 8.3 | 250 | 110 | 1 |
| Chevrolet Nova | 6 | 8.3 | 250 | 110 | 1 |
| Ford Pinto | 4 | 9.0 | 140 | 83 | 2 |

*All had automatic transmissions except for one of the 1977 Chevrolet Novas. All were 1977 models except the Ford Granada which was a 1976 model.

The gasoline used was Fuel B whose specifications were given earlier. The ratings were carried out in triplicate and the average octane number increase ($\Delta$ON) for the 9 cars is summarized below in terms of increase in octane numbers ($\Delta$ON) over the octane number of the base fuel. For comparison, the tests were also carried out using commercial manganese antiknock compound, methylcyclopentadienylmanganesetricarbonyl ("MMT"). The results demonstrate that the cobalt compounds provide outstanding antiknock performance under actual use conditions.

ROAD ANTIKNOCK PERFORMANCE
Nine-Car Average
Modified Uniontown Ratings in Triplicate
Base Fuel Road Octane Rating = 891.3

| Gms of metal per gallon | Road Octane Number Increase ($\Delta$ON) | |
|---|---|---|
| | "MMT" | Co(II) (HFAA)$_2$TMED |
| 0.025 | 0.48 | 0.84 |
| 0.050 | not determined | 1.45 |
| 0.10 | 1.40 | 1.99 |
| 0.20 | not determined | 2.61 |

EXAMPLES 34 TO 37

Antiknock performances of Ni(II) (HFAA)$_2$.TMED (Example 18), Ni(II) (HFAA)$_2$.HMPD (Example 19), Fe(II) (HFAA)$_2$.TMED (Example 15) and Fe(II) (HFAA)$_2$.HMPD (Example 16) were determined in Fuel B by the Research Method. The iron compounds of Examples 36 and 37 were tested for antiknock activity before they reacted with fuel impurities, i.e., they were tested within several hours of their introduction into the fuel. The results, summarized below, show that each of the compounds provide improvements in the octane rating of the fuel.

ANTIKNOCK PERFORMANCES
Grams of Metal/Gallon Compound
Research Octane Number Increase ($\Delta$ON)

| Ex. | 0.025 | 0.05 | 0.10 | 0.15 | 0.20 | 0.25 |
|---|---|---|---|---|---|---|
| | | | Ni(II) (HFAA)$_2$.TMED | S | | |
| 34 | 0.7 | 1.4 | 2.7 | 3.3 | 3.8 | 4.4 |
| | | | Ni(II) (HFAA)$_2$.HMPD | | | |
| 35 | 0.4 | 0.9 | 1.8 | 2.3 | 3.0 | 3.5 |
| | | | Fe(II) (HFAA)$_2$.TMED | | | |
| 36 | −0.7 | 0.9 | 1.1 | 1.4 | 1.6 | 2.1 |
| | | | Fe(II) (HFAA)$_2$.HMPD | | | |
| 37 | 0.4 | 0.6 | 0.9 | 0.8 | 1.1 | — |

EXAMPLE 38

Preparation of
Bis(difluoroacetylacetonyl)Cobalt(II).TMED

In a dry 250 ml reaction flask equipped with a stirrer, a condenser, gas inlet tube, an addition funnel, and a connection to a wet test meter to measure hydrogen evolution, were placed 60 ml of diethylether and 14.4 g of sodium hydride (50% in oil). The addition funnel was charged with a solution consisting of 29.7 g of difluoromethyl acetate, 17.4 g of dry acetone and 40 ml of dry diethylether. The reaction flask was cooled to 0° C. and the solution in the addition flask was added over a two-hour period. During the addition of difluoromethylacetate, evolution of 7.7 liters of hydrogen was noted. The reaction mixture was allowed to warm to room temperature and was stirred overnight under nitrogen atmosphere. A solution of 18 g of acetic acid in 120 ml of water was then added. The reaction mass changed from a light gray slurry to a two-phase liquid system consisting of an almost white ether layer and a dark brown clear aqueous layer. The aqueous layer was transferred to a 1 liter reaction flask and 33.6 gms of cobaltous acetate dissolved in 300 ml of water was added over a 30 minute period. The reaction mass was stirred for 30 minutes and 6.3 g of sodium carbonate was added, and the stirring was continued for an additional 30 minutes. The reaction mixture was filtered, and the precipitate was allowed to dry overnight. A 36.6 g (82%) yield of bis(difluoroacetylacetonyl)cobalt was obtained.

Bis(difluoroacetylacetonyl)cobalt, 34.7 g, was slurried in 500 ml of benzene in a 1 liter reaction flask equipped with a stirrer, a condenser, gas inlet tube, and an addition funnel. Tetramethylethylenediamine, 12.8 g, was then added over a 15 minute period. The reaction mass was heated to reflux for 4 hours during which time 4.2 ml of water was removed. The reaction mixture was cooled and filtered. Toluene was removed from the filtrate at 65° C. and 26 to 30 mm pressure providing 39.2 g (88% theory) of deep red oil which upon standing crystallized into brittle red solid. A 1 g sample was recrystallized in 3 ml of petroleum ether, providing 0.5 g of pink crystal which melted in the range of 83.5° to 84.5° C. Elemental analysis indicated that the compound contained 44.9% C, 6.0% H and 6.0% N; the theoretical values being 43.1% C, 5.8% H and 6.3% N.

EXAMPLE 39

Preparation of
Bis(chlorodifluoroacetylacetonyl)Cobalt(II).TMED

In a dry 250 ml reaction flask equipped with a stirrer, a condenser, gas inlet tube, an addition funnel, and a connection to a wet test meter to measure hydrogen evolution, were placed 40 ml of diethylether and 9.6 g of sodium hydride (50% in oil). The addition funnel was charged with a solution consisting of 28.5 g of ethylchlorodifluoroacetate, 11.6 g of dry acetone and 25 ml of diethylether. The reaction flask was cooled to 0° C. and the solution in the addition funnel was added over a three-hour period keeping the reaction temperature at 0° C.±2°. A total of 5.05 liters of hydrogen was evolved. After standing overnight at room temperature, 12 g of glacial acetic acid in 50 ml of water was added. The reaction mass turned from a gray slurry to a dark brown two-phase system. The reaction mass was transferred to a 500 ml reaction flask and a solution of 22.4 g of cobaltous acetate in 200 ml of water was added, dropwise. After stirring for 30 minutes, 4.2 g of sodium carbonate was added in portions. The reaction mass was filtered to yield 27.8 g (77% theory) of crude bis(chlorodifluoroacetylacetonyl)Co(II). A portion of the crude which was recrystallized from a toluene-petroleum ether mixture melted in the range of 181° to 183° C. Elemental analysis indicated that the chelate was a monohydrate: % C, 29.0; % H, 2.3; % Co, 14.1; with the theoretical values for the monohydrate being: % C, 28.8; % H, 2.4; and % Co, 14.2.

In a 1 liter reaction flask equipped with a thermometer, a condenser and an addition funnel, were placed 24.3 g of the above described bis(chlorodifluoroacetylacetonyl)Co(II) monohydrate and 500 ml of toluene. Tetramethylethylenediamine, 7.8 g, was added from the addition funnel over a ten-minute period. The reaction mixture was heated to reflux and kept on reflux until no more water separated. A total of 3 ml of water was collected. The reaction mixture was then filtered and the toluene removed at 60° to 70° C. under reduced pressure to provide 25.5 g of viscous ruby-red oil. Upon standing for a few days, most of the oil crystallized. Recrystallization from petroleum ether provided 15 g of material melting in the range of 71° to 72.5° C. Elemental analysis showed: % C, 38.9; % H, 4.7; % N, 5.5; and % Co, 11.5; with the theoretical values for bis(chlorodifluoroacetonyl)Co(II).TMED being: % C, 37.4; % H, 4.7; % N, 5.5; and % Co, 11.5.

EXAMPLES 40 TO 45

The following Examples concern compounds of the invention wherein different combinations of ligands $L_1$, $L_2$ and $L_3$ are used with cobalt as the metal. The preparation of these compounds was accomplished by combining cobalt ($M^{++}$) ions with the $\beta$-diketone ligands followed by combination thereof with ligand, $L_3$.

The compounds are described in the following Table wherein HFAA stands for hexafluoroacetylacetone and ligand, $L_3$, is described in terms of A-Z-B, and TGA is thermogravimetric analysis.

| Ex. | $L_1$ and $L_2$ | $L_3$ A | $L_3$ Z | $L_3$ B | m.p. °C. | TGA Temp. °C. | Volatilized |
|---|---|---|---|---|---|---|---|
| 40 | HFAA | $CH_3O$ | $CH_2CH_2$ | $OCH_3$ | 57–58 | 50–185 | 90 |
| 41 | HFAA | $CH_3O$ | $CH_2CH_2$ | $N(CH_3)_2$ | 72–73 | | |
| 42 | HFAA | $CH_3S$ | $CH_2CH_2$ | $N(CH_3)_2$ | 87–88 | 105–203 | 100 |
| 43 | HFAA | $C_2H_5S$ | $CH_2CH_2$ | $SC_2H_5$ | 57–59 | 120–207 | 90 |
| 44 | (thiophene-OCCH$_2$CO—CF$_3$) | $(CH_3)_2N$ | $CH_2CH_2$ | $N(CH_3)_2$ | 138–139 | 293 | 90 |
| 45 | HFAA | $NH_2$ | $C(CH_3)_2$—$(CH_3)_2C$ | $NH_2$ | 111–112 | 215 | 90 |

The compounds of Examples 38 to 43 give good octane ratings improvement in fuel as shown in the following Table wherein the fuel is Fuel A whose specifications appear, supra, preceding Example 1.

Antiknock Performance Of Representative Compounds in Fuel A

| Compound of (Ex. No.) | Gms of metal per gallon | Increase in Octane Number ($\Delta ON$) Research (R) | Motor (M) | (R + M)/2 |
|---|---|---|---|---|
| 38 | 0.025 | 0.7 | 014 | 0.6 |
|  | 0.05 | 1.3 | 0.7 | 1.0 |
|  | 0.10 | 1.8 | 1.1 | 1.5 |
|  | 0.20 | 2.7 | 1.5 | 2.1 |
|  | 0.30 | 3.5 | 1.6 | 2.6 |
| 39 | 0.025 | 0.8 | 0.3 | 0.6 |
|  | 0.05 | 1.2 | 0.6 | 0.9 |
|  | 0.10 | 1.5 | 0.8 | 1.1 |
|  | 0.20 | 2.4 | 1.4 | 1.9 |
|  | 0.30 | 2.5 | 1.6 | 2.1 |
| 40 | 0.025 | 0.6 | 0.4 | 0.5 |
|  | 0.05 | 0.8 | 0.7 | 0.8 |
|  | 0.10 | 1.6 | 0.9 | 1.3 |
|  | 0.15 | 2.0 | 1.1 | 1.6 |
|  | 0.20 | 2.5 | 1.3 | 1.9 |
|  | 0.30 | 3.2 | 1.8 | 2.5 |
| 41 | 0.025 | 1.1 | 0.5 | 0.8 |
|  | 0.05 | 1.9 | 0.8 | 1.4 |
|  | 0.10 | 2.6 | 1.5 | 2.1 |
|  | 0.15 | 3.2 | 1.8 | 2.5 |
|  | 0.20 | 3.6 | 2.0 | 2.8 |
|  | 0.30 | 4.4 | 2.3 | 3.4 |
| 42 | 0.025 | 1.0 | 0.2 | 0.6 |
|  | 0.5 | 1.7 | 0.5 | 1.1 |
|  | 0.10 | 2.4 | 0.9 | 1.7 |
|  | 0.15 | 2.9 | 1.2 | 2.1 |
|  | 0.20 | 3.1 | 1.3 | 2.2 |
|  | 0.30 | 4.1 | 1.6 | 2.9 |
| 43 | 0.025 | 0.6 | 0.3 | 0.5 |
|  | 0.05 | 0.9 | 0.6 | 0.8 |
|  | 0.10 | 1.6 | 0.6 | 1.1 |
|  | 0.15 | 1.6 | 1.2 | 1.4 |
|  | 0.20 | 1.9 | 1.1 | 1.5 |

The embodiments of the invention in which an exclusive property or privilege is claimed are defined as follows:

1. A compound having the structure

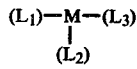

wherein
  M is a divalent metal selected from the group Mn, Fe, Co and Ni,
  $L_1$ and $L_2$ are the same or different chelate-forming β-diketone groups having from 5 to 20 carbon atoms, one or both of $L_1$ and $L_2$ having at least one polyfluoroalkyl group, —$CF_2X$, adjacent to the carbonyl group,
  X is selected from the group H, F, Cl, phenyl, $C_1$–$C_6$ alkyl and $C_nF_{2n}Y$,
  n is 1 to 6,
  Y is H, F, or Cl,
  $L_3$ is a ligand having the structure, A-Z-B,
wherein
  A and B are the same or different members of the group —$NH_2$, —$NHR_5$, —$NR_5R_6$, OH, $OR_5$, SH, $SR_5$ and $PR_5R_6$,
  $R_5$ and $R_6$ are the same or different members of the group $C_1$ to $C_4$ alkyl, and
  Z is a divalent hydrocarbyl group having 2 to 10 carbon atoms selected from a member of the group alkylene, phenylene and cycloalkylene, each member providing 2 or 3 carbon atoms between A and B, with the proviso that when Z is phenylene, the number of carbon atoms between A and B is 2.

2. A compound according to claim 1 wherein each of $L_1$ and $L_2$ is the difluoroacetylacetonyl β-diketone group.

3. A compound according to claim 1 wherein each of $L_1$ and $L_2$ is the chlorodifluoroacetylacetonyl β-diketone group.

4. A compound according to claim 1 wherein each of $L_1$ and $L_2$ is

Z is $CH_2CH_2$ and each of A and B is $N(CH_3)_2$.

5. A compound according to claim 1 wherein each of $L_1$ and $L_2$ is a hexafluoroacetylacetonyl β-diketone group.

6. A compound according to claim 5 wherein Z is $CH_2CH_2$.

7. A compound according to claim 6 wherein each of A and B is $CH_3O$.

8. A compound according to claim 6 wherein A is $CH_3O$ and B is $N(CH_3)_2$.

9. A compound according to claim 6 wherein A is $CH_3S$ and B is $N(CH_3)_2$.

10. A compound according to claim 6 wherein each of A and B is $SC_2H_5$.

11. A compound according to claim 6 wherein Z is $C(CH_3)_2C(CH_3)_2$ and each of A and B is $NH_2$.

12. A compound according to claim 1 having the structure

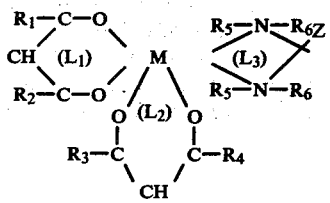

wherein:
  $R_1$, $R_2$, $R_3$, and $R_4$ are each individually selected from $C_1$ to $C_3$ perfluoroalkyl and $C_1$ to $C_6$ alkyl with at least one of $R_1$, $R_2$, $R_3$, and $R_4$ being a perfluoroalkyl group, and
  $R_5$ and $R_6$ are selected from hydrogen and $C_1$ to $C_4$ alkyl.

13. A compound according to claim 12 wherein M is selected from Co and Ni.

14. A compound according to claim 13 wherein M is Co.

15. A compound according to claim 13 wherein M is Ni.

16. A compound according to claim 12 wherein $R_1$, $R_2$, $R_3$, and $R_4$ are each $CF_3$.

17. A compound according to claim 12 wherein $R_5$ and $R_6$ are each $CH_3$.

18. A compound according to claim 12 wherein Z is —$C_2H_4$—.

19. A compound according to claim 16 wherein $R_5$ and $R_6$ are each $CH_3$ and Z is —$C_2H_4$—.

20. A compound according to claim 14 wherein each of $R_1$, $R_2$, $R_3$, and $R_4$ is $CF_3$, $R_5$ and $R_6$ are each $CH_3$ and Z is $C_2H_4$.

21. A compound according to claim 15 wherein each of $R_1$, $R_2$, $R_3$ and $R_4$ is $CF_3$, $R_5$ and $R_6$ are each $CH_3$ and Z is $C_2H_4$.

22. A compound according to claim 14 wherein $R_1$ and $R_3$ are each $(CH_3)_3C$, $R_2$ and $R_4$ are each $CF_3$, $R_5$ and $R_6$ are each $CH_3$ and Z is $C_2H_4$.

23. A compound according to claim 14 wherein $R_1$ and $R_3$ are each $CF_3$, $R_2$ and $R_4$ are each $CH_3$, $R_5$ and $R_6$ are each $CH_3$ and Z is $C_2H_4$.

24. A compound according to claim 14 wherein each of $R_1$, $R_2$, $R_3$, and $R_4$ is $CF_3$, $R_5$ and $R_6$ are each $CH_3$ and Z is $CH_2C(CH_3)_2CH_2$.

25. A compound according to claim 14 wherein $R_1$ and $R_2$ are each $CH_3$, $R_3$ and $R_4$ are each $CF_3$, $R_5$ and $R_6$ are each $CH_3$ and Z is $C_2H_4$.

26. A compound according to claim 14 wherein $R_1$ and $R_3$ are each $CH_3$, $R_2$ is $CH_3CH(CH_3)CH_2$, $R_4$ is $CF_3$, $R_5$ and $R_6$ are each $CH_3$ and Z is $C_2H_4$.

27. A compound according to claim 15 wherein $R_1$ and $R_3$ are each $CH_3$, $R_2$ and $R_4$ are each $CF_3$, $R_5$ and $R_6$ are each $CH_3$ and Z is $C_2H_4$.

28. A compound according to claim 15 wherein each of $R_1$, $R_2$, $R_3$ and $R_4$ is $CF_3$, $R_5$ and $R_6$ are each $CH_3$ and Z is $CH_2C(CH_3)_2CH_2$.

29. A concentrate comprising about 5% to 50% by weight of the compound of claim 1 in an organic solvent therefor.

30. A fuel composition comprising a fuel boiling in the gasoline boiling range containing an amount of a compound of claim 1 to provide at least about 0.01 gram of metal per gallon of fuel composition.

* * * * *